(12) United States Patent
Laricchia et al.

(10) Patent No.: US 10,343,987 B2
(45) Date of Patent: Jul. 9, 2019

(54) PROCESS FOR OXIDIZING ONE OR MORE THIOL COMPOUNDS

(71) Applicant: UOP LLC, Des Plaines, IL (US)

(72) Inventors: Luigi Laricchia, Arlington Heights, IL (US); Edward F. Smith, Roselle, IL (US); Jonathan A. Tertel, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/863,752

(22) Filed: Jan. 5, 2018

(65) Prior Publication Data

US 2018/0201575 A1    Jul. 19, 2018

Related U.S. Application Data

(63) Continuation of application No. PCT/US2016/039520, filed on Jun. 27, 2016.

(60) Provisional application No. 62/189,988, filed on Jul. 8, 2015.

(51) Int. Cl.
| | | |
|---|---|---|
| *C07C 319/24* | (2006.01) | |
| *C07C 319/28* | (2006.01) | |
| *B01J 19/24* | (2006.01) | |
| *B01D 19/00* | (2006.01) | |
| *C10G 70/04* | (2006.01) | |

(52) U.S. Cl.
CPC ........ *C07C 319/24* (2013.01); *B01D 19/0005* (2013.01); *B01J 19/24* (2013.01); *C07C 319/28* (2013.01); *C10G 70/04* (2013.01)

(58) Field of Classification Search
CPC ..... C07C 319/24; C07C 319/28; C10G 70/04; B01J 19/24; B01D 19/0005
See application file for complete search history.

(56) References Cited

U.S. PATENT DOCUMENTS

| | | | |
|---|---|---|---|
| 4,090,954 A | 5/1978 | Ward | |
| 7,326,333 B2 * | 2/2008 | Laricchia | B01D 11/043 208/226 |
| 8,597,501 B2 | 12/2013 | Krupa et al. | |
| 2012/0043259 A1 | 2/2012 | Norton | |
| 2014/0197109 A1 | 7/2014 | Laricchia et al. | |
| 2014/0202963 A1 | 7/2014 | Laricchia et al. | |

(Continued)

FOREIGN PATENT DOCUMENTS

| | | |
|---|---|---|
| CN | 102671907 A | 9/2012 |
| CN | 104263403 A | 1/2015 |

OTHER PUBLICATIONS

Search Report dated Jun. 27, 2016 for corresponding PCT Appl. No. PCT/US2016/039520.

*Primary Examiner* — Rosalynd A Keys

(57) ABSTRACT

A process and apparatus for oxidizing thiol compounds from an alkaline stream. The process includes passing a thiol rich alkaline stream and an oxygen containing gas to a low pressure oxidizing zone to oxidize at least a portion of the thiol compounds to disulfide compounds. A liquid stream comprising the alkali containing the disulfide compounds is passed through a pump to increase the pressure and form a pressurized alkaline stream. The pressurized alkaline stream and a sulfur lean liquid light hydrocarbon stream are introduced to a high pressure disulfide separation vessel to form a sulfur lean alkaline stream and a sulfur rich liquid light hydrocarbon stream.

17 Claims, 1 Drawing Sheet

(56) References Cited

U.S. PATENT DOCUMENTS

2014/0235897 A1    8/2014   Tertel et al.
2014/0371509 A1   12/2014   Laricchia et al.

* cited by examiner

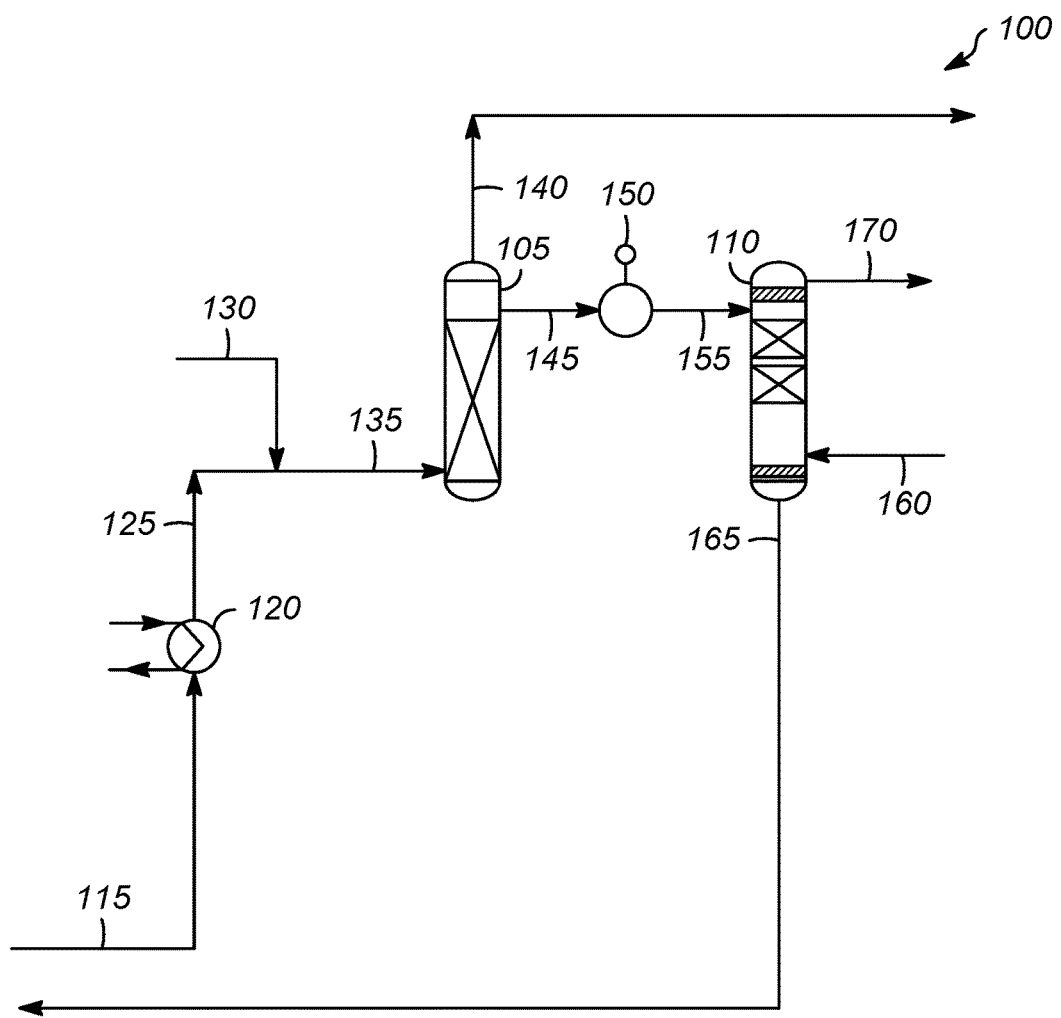

PROCESS FOR OXIDIZING ONE OR MORE THIOL COMPOUNDS

CROSS-REFERENCE TO RELATED APPLICATIONS

This application is a Continuation of International Application No. PCT/US2016/039520 filed Jun. 27, 2016 which application claims benefit of U.S. Provisional Application No. 62/189,988 filed Jul. 8, 2015, the contents of which cited applications are hereby incorporated by reference in their entirety.

BACKGROUND OF THE INVENTION

A sulfur removal process can extract mercaptan from a hydrocarbon stream to a caustic stream. In a sulfur extraction unit, alkali extracts mercaptan from a hydrocarbon stream. These mercaptides may then be oxidized to disulfides by adding air and catalyst, and running the stream through an oxidizer.

In sulfur extraction units, a regenerated alkali stream is often used. The mercaptides in the alkali may be converted in the presence of oxygen to disulfides in an oxidizer. These three phases, spent air, lean alkali, and disulfide oil, can then be separated in a disulfide separator. Frequently, the alkali may further be contacted with a hydrocarbon to separate more disulfide oil from the alkali, requiring another vessel. This vessels may require increased plot space. Moreover, the disulfide oil can be sent from the disulfide separator to a filter or water wash to remove entrained alkali prior to being sent to downstream processing.

In some processes, the alkali regeneration section operates at a pressure between about 280 kPa (g) to about 410 kPa (g) (about 40 to about 60 psig) and a temperature between about 43° C. and about 54° C. (about 110 to about 130° F.). However, the alkaline needs to be returned to the extractor at a pressure of about 690 kPa (g) to about 2410 kPa (g) (about 100 to about 350 psig). Consequently, there are alkali circulating pumps positioned downstream of the disulfide separator vessel.

Wash oil is often necessary to obtain low sulfur liquefied petroleum gas (LPG) product from the sulfur extraction process (e.g., less than 5 wppm S). The use of lighter hydrocarbons (e.g., butane or lighter) as the wash oil source is precluded because much of it would vaporize at this operating pressure and temperature. However, in some locations, such as a gas plant, the only source of wash oil would be these lighter hydrocarbons.

Thus, it would be desirable to provide a caustic regeneration process which would allow the use of lighter hydrocarbon as the wash oil.

SUMMARY OF THE INVENTION

One aspect of the invention is a process for oxidizing thiol compounds from an alkaline stream. In one embodiment, the process includes passing a thiol rich alkaline stream and an oxygen containing gas to a low pressure oxidizing zone to oxidize at least a portion of the thiol compounds to disulfide compounds. A liquid stream comprising the alkali containing the disulfide compounds is passed through a pump to increase the pressure of the liquid stream comprising the alkali containing the disulfide compounds and form a pressurized alkaline stream containing the disulfide compounds. The pressurized alkaline stream containing the disulfide compounds and a sulfur lean liquid light hydrocarbon stream are introduced to a high pressure disulfide separation vessel to form a sulfur lean alkaline stream and a sulfur rich liquid light hydrocarbon stream.

Another aspect of the invention is an apparatus. In one embodiment, the apparatus includes a low pressure oxidizing zone having an inlet, and a liquid and vapor outlet. There is a pump having an inlet and an outlet, the pump inlet is in fluid communication with the oxidizing zone liquid outlet. The apparatus also includes a high pressure counter-current disulfide separation vessel having an alkali inlet at or near the top of the disulfide separation vessel, an alkali outlet at or near the bottom of the disulfide separation vessel, a wash oil inlet at or near the bottom of the disulfide separation vessel, and a wash oil outlet at or near the top of the disulfide separation vessel, the alkali inlet being in fluid communication with the pump outlet.

BRIEF DESCRIPTION OF THE DRAWING

The FIGURE is an illustration of one embodiment of a process according to the claimed invention.

DETAILED DESCRIPTION OF THE INVENTION

The present invention solves this need by providing a caustic regeneration process in which light hydrocarbons can be used as the wash oil. This is accomplished by including a caustic circulation pump between a low pressure oxidizing zone and high pressure disulfide separation vessel. The oxidizing zone operates at the lower optimal pressure of about 210 kPa (g) to about 550 kPa (g) (about 30 to about 80 psig), while the high pressure disulfide separation vessel operates at a higher pressure of about 690 kPa(g) to about 2760 kPa(g) (about 100 to about 400 psig).

These operating conditions allow liquid light hydrocarbons, such as LPG, $C_4$ hydrocarbons, or even $C_3$ hydrocarbons, to be used as the wash oil for the alkali regeneration process.

Referring to the FIGURE, an exemplary apparatus 100 is depicted, which may include an oxidation vessel 105 and a high pressure disulfide separation vessel 110. Typically, the apparatus 100 receives an alkaline stream 115 including one or more thiol compounds.

The alkaline stream 115 is typically a rich caustic stream including one or more mercaptides. The rich caustic can be obtained from an extraction zone (not shown) to remove sulfur compounds from one or more hydrocarbons, such as one or more $C_2$-$C_8$ hydrocarbons. Such exemplary extraction zones are disclosed in, e.g., US 2012/0000826.

In some embodiments, the alkaline stream 115 is heated in a heat exchanger or other suitable heater 120 to form a heated alkaline stream 125.

The heated alkaline stream 125 can be mixed with an oxygen-containing gas 130, often air. Afterwards, a mixed stream 135 comprising the heated alkaline stream 125 and the oxygen-containing gas 130, such as air, enters the oxidation vessel 105. Alternatively, the heated alkaline stream 125 and the oxygen-containing gas 130 can enter the oxidation vessel 105 separately.

The oxidation vessel 105 can include a distributor, one or more packing elements, a level indicator, and a baffle, for example. Typically, the distributor can be any suitable device, such as a ring distributor or an elongated pipe forming a series of holes. The one or more packing elements can include any suitable packing, such as at least one of ring packing, such as one or more carbon or stainless steel rings, a fiber contactor, a film contactor, one or more trays, and a mesh, to increase the surface area for improving contact between the rich caustic, catalyst, and the oxygen-containing gas. One exemplary ring packing can include rings sold under the trade designation RASCHIG by Raschig GmbH of Ludwigshafen, Germany. Alternatively, the carbon rings or a carbon bed can be impregnated with a metal phthalocyanine catalyst, as disclosed in, e.g., U.S. Pat. Nos. 4,318,825 and 5,207,927.

The oxidizing zone operates at a pressure of about 210 kPa (g) to about 550 kPa (g) (about 30 to about 80 psig), or about 280 kPa (g) to about 410 kPa (g) (about 40 to about 60 psig), and a temperature of about 38° C. to about 60° C., or about 43° C. to about 55° C.

In some embodiments, the mixed stream 135 enters at or near the bottom of the oxidation vessel 105 and flows upward through an upflow packed bed oxidizing zone. The thiol compounds are oxidized to disulfide compounds in the oxidation vessel 105. Other flow arrangements are possible as would be understood by those of skill in the art. The distributor is typically located about 0.3 m (one ft) above the bottom tangent of the vessel. If the oxygen containing gas and the liquid enter separately, the gas would added at the height of the distributor, and the liquid would enter through a nozzle in the bottom head of the vessel. By at or near the bottom we mean that the stream enters in the bottom 30% of the column, or the bottom 25%, or the bottom 20%, or the bottom 15%, or the bottom 10%, or the bottom 5%.

A non-soluble vapor stream 140 is separated from the liquid stream 145 comprising the alkali containing the disulfide compounds and exits from the top of the oxidation vessel 105. The vapor stream 140 can be further processed as needed (not shown).

In some embodiments, the liquid stream 145 comprising the alkali containing the disulfide compounds exits at or near the top of the oxidation vessel 105. The liquid is withdrawn from a sump in an accumulator tray (i.e., below the liquid/vapor interface) which is typically located about 1.2 m (4 ft) from the top tangent of the vessel. By at or near the top we mean that the stream is in the top 30% of the column, or the top 25%, or the top 20%, or the top 15%, or the top 10%.

The liquid stream 145 comprising the alkaline containing the disulfide compounds is sent to pump 150 to increase the pressure of the stream to the operating pressure of the high pressure disulfide separation vessel 110. Suitable pumps include, but are not limited to, seal or seal-less centrifugal type of pumps.

The pressurized stream 155 is sent to the high pressure disulfide separation vessel 110. The high pressure disulfide separation vessel 110 operates at a higher pressure than the oxidation vessel 105 of about 690 kPa(g) to about 2760 kPa(g) (about 100 to about 400 psig), or about 1030 kPa (g) to about 2410 kPa (g) (about 150 to about 350 psig), and a temperature of about 30° C. to about 70° C., or about 40° C. to about 60° C.

In some embodiments, the pressurized stream 155 comprising the alkali containing the disulfide compounds enters near the top of the high pressure disulfide separation vessel 110, and a sulfur lean liquid light hydrocarbon stream 160 is introduced near the bottom of the high pressure disulfide separation vessel 110. The stream comprising alkali containing the disulfide compounds enters above the packed bed section near the top of the vessel, while the sulfur lean liquid light hydrocarbon stream enters below the packed bed section near the bottom of the vessel. By near the top we mean that the stream is in the top 30% of the column, or the top 25%, or the top 20%. By near the bottom we mean that the stream exits in the bottom 30% of the column, or the bottom 25%, or the bottom 20%. Suitable sulfur lean liquid light hydrocarbon streams include, but are not limited to, butane, propane, ethane, liquefied petroleum gas, or combinations thereof The sulfur lean liquid light hydrocarbon stream 160 flow rate would typically be between about 2 to about 20 vol % of the flow rate of the alkali containing the disulfide compounds, or about 5 to about 15 vol %. It could also be the product of the extractor that is included in the extraction unit (not shown) attached to this regeneration section. The sulfur lean liquid light hydrocarbon stream 160 could not be used to wash the spent air due to vaporization losses.

The alkali containing the disulfide compounds flows downward, while the sulfur lean liquid light hydrocarbon flows upward in a counter-current arrangement across a packed bed, or trays, or other contacting devices. Other flow arrangements are possible as would be understood by those of skill in the art.

The disulfide compounds are transferred from the alkali to the liquid light hydrocarbon forming a sulfur lean alkaline stream 165 and a sulfur rich liquid light hydrocarbon stream 170. In some embodiments, the sulfur lean alkaline stream 165 exits at the bottom of the high pressure disulfide separation vessel 110 (typically as close to the bottom tangent line as possible, e.g., less than 0.5 m), and the sulfur rich liquid light hydrocarbon stream 170 exits at the top of the high pressure disulfide separation vessel 110 (typically as close to the top tangent line as possible, e.g., less than 0.5 m).

The sulfur lean alkaline stream 165 can be recycled to the extractor (not shown) from which the thiol rich alkaline stream 115 came.

The sulfur rich liquid light hydrocarbon stream 170 can be treated as needed (not shown).

In some embodiments, the high pressure disulfide separation vessel 110 can be divided into one or more chambers (not shown), if desired. In some embodiments, there are two chambers. The first chamber can include one or more packed beds and one or more distributors. Generally, the one or more packed beds can include any number of suitable beds, such as one to four beds. The packed beds can include any suitable packing, such as a structured packing, such as structured metal vapor packing, or a random packing obtained from, e.g., Koch-Glitsch, LP of Wichita, Kans. In addition, the high pressure disulfide separation vessel 110 can include one or more coalescers, which can include one or more coalescing elements, such as at least one of a metal mesh that is optionally coated, one or more glass fibers, sand, or anthracite coal. In one exemplary embodiment, the coalescer can include a coated mesh. Desirably, the coating may be an oleophobic and/or hydrophilic coating usually suited for an oil phase. One exemplary mesh may include a coating sold under the trade designation COALEX or KOCH-OTTO YORK™ separations technology by Koch-Glitsch, LP of Wichita, Kans. Alternatively, the mesh can include stainless steel or fiberglass. The distributors can take any suitable form, such as a ring or an elongated pipe forming one or more holes.

The second chamber can include a lower end and can contain a coalescer. The coalescer may include one or more coalescing elements, such as at least one of a metal mesh that is optionally coated, one or more glass fibers, sand, or anthracite coal. In one exemplary embodiment, the coalescer can include a coated mesh. Desirably, the coating may be an oleophilic and/or hydrophobic coating usually suited for an aqueous phase. Such a coating may include at least one of a fluoropolymer and polypropylene. Suitable fluoropolymers can include one or more of polytetrafluoroethylene, fluorinated ethylene-propylene, perfluoroalkoxy, and ethylene tetrafluoroethylene. Exemplary fluoropolymers are disclosed in U.S. Pat. Nos. 5,456,661 and 2,230,654.

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1, C_2, C_3 \ldots C_n$ where "n" represents the number of carbon atoms in the one or more hydrocarbon molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three carbon atoms and/or more. In addition, the term "stream" may be applicable to other fluids, such as aqueous and non-aqueous solutions of alkali or basic compounds, such as sodium hydroxide.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 50%, and preferably about 70%, by weight, of a compound or class of compounds in a stream. If referring to a solute in solution, e.g., one or more disulfide compounds in an alkaline solution, the term "rich" may be referenced to the equilibrium concentration of the solute. As an example, about 5%, by mole, of a solute in a solvent may be considered rich if the concentration of solute at equilibrium is 10%, by mole.

As used herein, the term "substantially" can mean an amount of at least generally about 80%, preferably about 90%, and optimally about 99%, by weight, of a compound or class of compounds in a stream.

As used herein, the term "coupled" can mean two items, directly or indirectly, joined, fastened, associated, connected, or formed integrally together either by chemical or mechanical means, by processes including stamping, molding, or welding. What is more, two items can be coupled by the use of a third component such as a mechanical fastener, e.g., a screw, a nail, a bolt, a staple, or a rivet; an adhesive; or a solder.

As used herein, the term "coalescer" may be a device containing glass fibers or other material to facilitate separation of immiscible liquids of similar density.

As used herein, the term "immiscible" can mean two or more phases that cannot be uniformly mixed or blended.

As used herein, the term "phase" may mean a liquid, a gas, or a suspension including a liquid and/or a gas, such as a foam, aerosol, or fog. A phase may include solid particles. Generally, a fluid can include one or more gas, liquid, and/or suspension phases.

As used herein, the term "alkali" can mean any substance that in solution, typically a water solution, has a pH value greater than about 7.0, and exemplary alkali can include sodium hydroxide, potassium hydroxide, or ammonia. Such an alkali in solution may be referred to as "an alkaline solution" or "an alkali" and includes caustic, i.e., sodium hydroxide in water.

As used herein, the term "parts per million" may be abbreviated herein as "ppm" and "weight ppm" may be abbreviated herein as "wppm".

As used herein, the term "mercaptan" typically means thiol and may be used interchangeably therewith, and can include compounds of the formula RSH as well as salts thereof, such as mercaptides of the formula $RS^-M^+$ where R is a hydrocarbon group, such as an alkyl or aryl group, that is saturated or unsaturated and optionally substituted, and M is a metal, such as sodium or potassium.

As used herein, the term "disulfides" can include dimethyldisulfide, diethyldisulfide, and ethylmethyldisulfide, and possibly other species having the molecular formula RSSR' where R and R' are each, independently, a hydrocarbon group, such as an alkyl or aryl group, that is saturated or unsaturated and optionally substituted. Typically, a disulfide is generated from the oxidation of a mercaptan-containing caustic and forms a separate hydrocarbon phase that is not soluble in the aqueous caustic phase. Generally, the term "disulfides" as used herein excludes carbon disulfide ($CS_2$).

As used herein, the weight percent or ppm of sulfur, e.g., "wppm-sulfur" is the amount of sulfur, and not the amount of the sulfur-containing species unless otherwise indicated. As an example, methylmercaptan, $CH_3SH$, has a molecular weight of 48.1 with 32.06 represented by the sulfur atom, so the molecule is about 66.6%, by weight, sulfur. As a result, the actual sulfur compound concentration can be higher than the wppm-sulfur from the compound. An exception is that the disulfide content in caustic can be reported as the wppm of the disulfide compound.

As used herein, the term "lean alkali" is an alkali having been treated and having desired levels of sulfur, including one or more mercaptans and one or more disulfides for treating one or more $C_1$-$C_5$ hydrocarbons in an extraction zone.

As used herein, the term "regeneration" with respect to a solvent stream can mean removing one or more disulfide sulfur species from the solvent stream to allow its reuse.

As used herein, the term "about" means within 10% of the value, or within 5%, or within 1%.

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a process for oxidizing thiol compounds from an alkaline stream comprising passing a thiol rich alkaline stream and an oxygen containing gas to a low pressure oxidizing zone to oxidize at least a portion of the thiol compounds to disulfide compounds; passing a liquid stream comprising the alkali containing the disulfide compounds through a pump to increase the pressure of the liquid stream comprising the alkali containing the disulfide compounds and form a pressurized alkaline stream containing the disulfide compounds; and introducing the pressurized alkaline stream containing the disulfide compounds and a sulfur lean liquid light hydrocarbon stream to a high pressure separator to form a sulfur lean alkaline stream and a sulfur rich liquid light hydrocarbon stream. An embodiment of the invention is one, any or all of prior embodiments in this paragraph up through the first embodiment in this paragraph further comprising separating a non-soluble vapor stream from a liquid stream comprising the alkali containing the disulfide compounds before passing the liquid stream comprising the alkali containing the disulfide compounds through the pump. An embodiment of the invention is one, any or all of prior embodiments in this paragraph up through the first embodiment in this paragraph wherein the sulfur lean liquid light hydrocarbon stream is butane, propane, ethane, liquefied petroleum gas, or combinations thereof. An embodiment of the invention is one, any or all of prior embodiments in this paragraph up through the first embodiment in this paragraph wherein the oxidizing zone is operated at a pressure of about 210 kPa (g) to about 550 kPa (g). An embodiment of the invention is one, any or all of prior embodiments in this paragraph up through the first embodiment in this paragraph wherein the separator is operated at a pressure of about 690 kPa(g) to about 2760 kPa(g). An embodiment of the invention is one, any or all of prior embodiments in this paragraph up through the first embodiment in this paragraph wherein the separator has a counter-current flow. An embodiment of the invention is one, any or all of prior embodiments in this paragraph up through the first embodiment in this paragraph wherein the pressurized alkaline stream containing the disulfide compounds is introduced near the top of the separator, and the sulfur lean liquid light hydrocarbon stream is introduced near the bottom of the separator. An embodiment of the invention is one, any or all of prior embodiments in this paragraph up through the first embodiment in this paragraph wherein the thiol rich alkaline stream and the oxygen-containing gas are mixed before being passed to the oxidizing zone. An embodiment of the invention is one, any or all of prior embodiments in this paragraph up through the first embodiment in this paragraph wherein the oxygen-containing gas comprises air. An embodiment of the invention is one, any or all of prior embodiments in this paragraph up through the first embodiment in this paragraph wherein a flow rate of the sulfur lean liquid light hydrocarbon stream is about 2 to about 20 vol % of a flow rate of the pressurized oxidized alkaline stream. An embodiment of the invention is one, any or all of prior embodiments in this paragraph up through the first embodiment in this paragraph wherein the oxidizing zone is operated at a temperature of about 38° C. to about 60° C. An embodiment of the invention is one, any or all of prior embodiments in this paragraph up through the first embodiment in this paragraph further comprising heating the thiol rich alkaline stream before passing the thiol rich alkaline stream to the oxidizing zone. The process if claim 1 wherein the oxidizing zone is an upflow packed bed oxidizing zone.

A second embodiment of the invention is a process for oxidizing thiol compounds from an alkaline stream comprising passing a thiol rich alkaline stream and an oxygen containing gas to a low pressure upflow packed bed oxidizing zone at a pressure of about 210 kPa(g) to about 550 kPa(g) to oxidize at least a portion of the thiol compounds to disulfide compounds; separating a non-soluble vapor stream from a liquid stream comprising the alkali containing the disulfide compounds; passing the liquid stream comprising the alkali containing the disulfide compounds through a pump to increase the pressure of the liquid stream comprising alkali containing the disulfide compounds and form a pressurized alkaline stream containing the disulfide compounds; and introducing the pressurized alkaline stream containing the disulfide compounds and a sulfur lean liquid light hydrocarbon stream to a high pressure counter-current separator at a pressure of about 690 kPa(g) to about 2760 kPa(g) to form a sulfur lean alkaline stream and a sulfur rich liquid light hydrocarbon stream, wherein the sulfur lean liquid light hydrocarbon stream comprises butane, propane, ethane, liquefied petroleum gas, or combinations thereof. An embodiment of the invention is one, any or all of prior embodiments in this paragraph up through the second embodiment in this paragraph wherein the thiol rich alkaline stream and the oxygen-containing gas are mixed before being passed to the oxidizing zone. An embodiment of the invention is one, any or all of prior embodiments in this paragraph up through the second embodiment in this paragraph wherein a flow rate of the liquid light hydrocarbon stream is about 2 to about 20 vol % of a flow rate the pressurized alkaline stream containing the disulfide compounds. An embodiment of the invention is one, any or all of prior embodiments in this paragraph up through the second embodiment in this paragraph wherein the sulfur lean liquid light hydrocarbon stream is butane, propane, ethane, liquefied petroleum gas, or combinations thereof.

A third embodiment of the invention is an apparatus comprising a low pressure oxidizing zone having an inlet, and a liquid outlet; a pump having an inlet and an outlet, the pump inlet in fluid communication with the oxidizing zone liquid outlet; and a high pressure counter-current separator having an alkali inlet near the top of the separator, an alkali outlet at the bottom of the separator, a wash oil inlet near the bottom of the separator, and a wash oil outlet at the top of the separator, the alkali inlet in fluid communication with the pump outlet. An embodiment of the invention is one, any or all of prior embodiments in this paragraph up through the third embodiment in this paragraph wherein the oxidizing zone inlet is in fluid communication with a sulfur rich alkali outlet of an extraction zone, and wherein the alkali outlet of the separator is in fluid communication with a sulfur lean alkali inlet of the extraction zone. An embodiment of the invention is one, any or all of prior embodiments in this paragraph up through the third embodiment in this paragraph wherein the wash oil inlet is in fluid communication with a source of liquid light hydrocarbon.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed:

1. A process for oxidizing thiol compounds from an alkaline stream comprising:
    passing a thiol rich alkaline stream and an oxygen containing gas to a low pressure oxidizing zone to oxidize at least a portion of the thiol compounds to disulfide compounds to form a liquid stream comprising the alkali containing the disulfide compounds;
    passing the liquid stream from the low pressure oxidizing zone through a pump to increase the pressure of the liquid stream and form a pressurized alkaline stream containing the disulfide compounds; and
    introducing the pressurized alkaline stream containing the disulfide compounds and a sulfur lean liquid light hydrocarbon stream to a high pressure disulfide separation vessel to form a sulfur lean alkaline stream and a sulfur rich liquid light hydrocarbon stream.

2. The process of claim 1 further comprising separating a non-soluble vapor stream from the liquid stream from the low pressure oxidizing zone before passing the liquid stream from the low pressure oxidizing zone through the pump.

3. The process of claim 1 wherein the sulfur lean liquid light hydrocarbon stream is butane, propane, ethane, liquefied petroleum gas, or combinations thereof.

4. The process of claim 1 wherein the oxidizing zone is operated at a pressure of about 210 kPa (g) to about 550 kPa (g).

5. The process of claim 1 wherein the disulfide separation vessel is operated at a pressure of about 690 kPa(g) to about 2760 kPa(g).

6. The process of claim 1 wherein the disulfide separation vessel has a counter-current flow.

7. The process of claim 5 wherein the pressurized alkaline stream containing the disulfide compounds is introduced near the top of the disulfide separation vessel, and the sulfur lean liquid light hydrocarbon stream is introduced near the bottom of the disulfide separation vessel.

8. The process of claim 1 wherein the thiol rich alkaline stream and the oxygen-containing gas are mixed before being passed to the oxidizing zone.

9. The process of claim 1 wherein the oxygen-containing gas comprises air.

10. The process of claim 1 wherein a flow rate of the sulfur lean liquid light hydrocarbon stream is about 2 to about 20 vol % of a flow rate of the pressurized oxidized alkaline stream.

11. The process of claim 1 wherein the oxidizing zone is operated at a temperature of about 38° C. to about 60° C.

12. The process of claim 1 further comprising heating the thiol rich alkaline stream before passing the thiol rich alkaline stream to the oxidizing zone.

13. The process if claim 1 wherein the oxidizing zone is an upflow packed bed oxidizing zone.

14. A process for oxidizing thiol compounds from an alkaline stream comprising:
    passing a thiol rich alkaline stream and an oxygen containing gas to a low pressure upflow packed bed oxidizing zone at a pressure of about 210 kPa(g) to about 550 kPa(g) to oxidize at least a portion of the thiol compounds to disulfide compounds to form a liquid stream comprising the alkali containing the disulfide compounds;
    separating a non-soluble vapor stream from the liquid stream forming a reduced vapor liquid stream comprising the alkali containing the disulfide compounds;
    passing the reduced vapor liquid stream through a pump to increase the pressure of the reduced vapor liquid stream and form a pressurized alkaline stream containing the disulfide compounds; and
    introducing the pressurized alkaline stream containing the disulfide compounds and a sulfur lean liquid light hydrocarbon stream to a high pressure counter-current disulfide separation vessel at a pressure of about 690 kPa(g) to about 2760 kPa(g) to form a sulfur lean alkaline stream and a sulfur rich liquid light hydrocarbon stream, wherein the sulfur lean liquid light hydrocarbon stream comprises butane, propane, ethane, liquefied petroleum gas, or combinations thereof.

15. The process of claim 14 wherein the thiol rich alkaline stream and the oxygen-containing gas are mixed before being passed to the oxidizing zone.

16. The process of claim 14 wherein a flow rate of the liquid light hydrocarbon stream is about 2 to about 20 vol % of a flow rate the pressurized alkaline stream containing the disulfide compounds.

17. The process of claim 14 wherein the sulfur lean liquid light hydrocarbon stream is butane, propane, ethane, liquefied petroleum gas, or combinations thereof.

* * * * *

UNITED STATES PATENT AND TRADEMARK OFFICE
CERTIFICATE OF CORRECTION

PATENT NO.         : 10,343,987 B2
APPLICATION NO.    : 15/863752
DATED              : July 9, 2019
INVENTOR(S)        : Luigi Laricchia, Edward F. Smith and Jonathan A. Tertel Page 1 of 1

It is certified that error appears in the above-identified patent and that said Letters Patent is hereby corrected as shown below:

In the Specification

Column 1, Line 29, delete "This" and insert, --These--

Column 8, Lines 1-2, delete "if claim 1"

In the Claims

Column 10, Line 42, Claim 16, add "of" between "of a flow rate" and "the pressurized alkaline"

Signed and Sealed this
Second Day of June, 2020

Andrei Iancu
*Director of the United States Patent and Trademark Office*